US00PP26164P3

(12) United States Plant Patent
Babikow

(10) Patent No.: US PP26,164 P3
(45) Date of Patent: Nov. 24, 2015

(54) ***STOKESIA LAEVIS* PLANT NAMED 'DIVINITY'**

(50) Latin Name: *Stokesia laevis*
Varietal Denomination: Divinity

(71) Applicant: Paul David Babikow, Pensacola, FL (US)

(72) Inventor: Paul David Babikow, Pensacola, FL (US)

(73) Assignee: Emerald Coast Growers, LLC, Pensacola, FL (US)

( * ) Notice: Subject to any disclaimer, the term of this patent is extended or adjusted under 35 U.S.C. 154(b) by 9 days.

(21) Appl. No.: 13/815,391

(22) Filed: Apr. 29, 2013

(65) Prior Publication Data
US 2014/0325725 P1 Oct. 30, 2014

(51) Int. Cl.
*A01H 5/02* (2006.01)

(52) U.S. Cl.
USPC ..... Plt./484
CPC ..... *A01H 5/025* (2013.01)

(58) Field of Classification Search
USPC ..... Plt./484
CPC ..... A01H 5/02
See application file for complete search history.

*Primary Examiner* — Keith O. Robinson
(74) *Attorney, Agent, or Firm* — J. Nevin Shaffer, Jr.

(57) ABSTRACT

A new and distinct, vigorous cultivar of *Stokesia laevis* named 'Divinity', characterized by a compact growth habit, wide strap like leaves, and numerous white flowers.

3 Drawing Sheets

BACKGROUND OF THE INVENTION

The present invention relates to a new and distinct cultivar botanically known as *Stokesia laevis* and hereinafter referred to by the name 'Divinity'. 'Divinity' is a new and distinct cultivar found as a chance seedling in summer 2009 at a plant nursery in Pensacola, Fla. Asexual propagation in the form of division, root cuttings, and layering have all yielded successive generations exhibiting the same phenotypic characteristics of the original plant showing the new plant to be stable and reproducible in production.

SUMMARY OF THE INVENTION

Plants of the new *Stokesia laevis* have not been observed under all possible environmental conditions. The phenotype may vary somewhat with variations in environment such as temperature and light intensity without, however, any variance in genotype.

'Divinity' is a vigorous growing cultivar that produces large white flowers throughout the growing season. Multiple flowers are held above a compact mound of green foliage. It has proven to be easily propagated asexually.

The following traits have been repeatedly observed and are determined to be the unique characteristics of 'Divinity'. These characteristics in combination distinguish 'Divinity' as a new and distinct plant.

1. Large white flowers that open with a hint of yellow in the center that fades to white as the flower matures.
2. Wide strap-like leaves.
3. Compact mounding growth habit.
4. Easily propagated.
5. Flowers throughout the growing season.

The closest known *Stokesia laevis* cultivars are 'Mary Gregory' (unpatented), 'White Surprise' (unpatented), and 'Colorwheel' U.S. Plant Pat. No. 12,718. Applicant has made the following observations of the known similar cultivars as set forth in Table 1.

TABLE 1

| | 'Divinity' | 'White Surprise' | 'Colorwheel' | 'Mary Gregory' | Species |
|---|---|---|---|---|---|
| Height (cm) | 25-30 | 50 | 20-25 | 30-45 | 30-60 |
| Width (cm) | 50-55 | 45 | 60-66 | 30-45 | 30-45 |
| Leaf Width (cm) | 4-5 | 2-3 | .8-5 | 2-4 | 1-3 |
| Leaf Length (cm) | 25-30 | 16-18 | 15-25 | 20 | 15-25 |
| Flower dia. (cm) | 8-10 | 5-10 | 5-10 | 7-10 | 5-8 |
| Flower Color | White-Light Yellow | White | White-Light Purple-Dark Purple (White Center) | Yellow | Blue-Purplish Blue |
| Growth Habit | mounding | Round Clump | mounding | mounding | Upright |

DESCRIPTION OF THE PHOTOGRAPHS

The accompanying colored photographs illustrate the overall appearance of the new plant showing the colors as true as it is reasonably possible to obtain in colored reproductions of this type. Colors in the photographs may differ slightly from the color values cited in the detailed botanical description which accurately describe the colors of the new plant.

Figure 1:
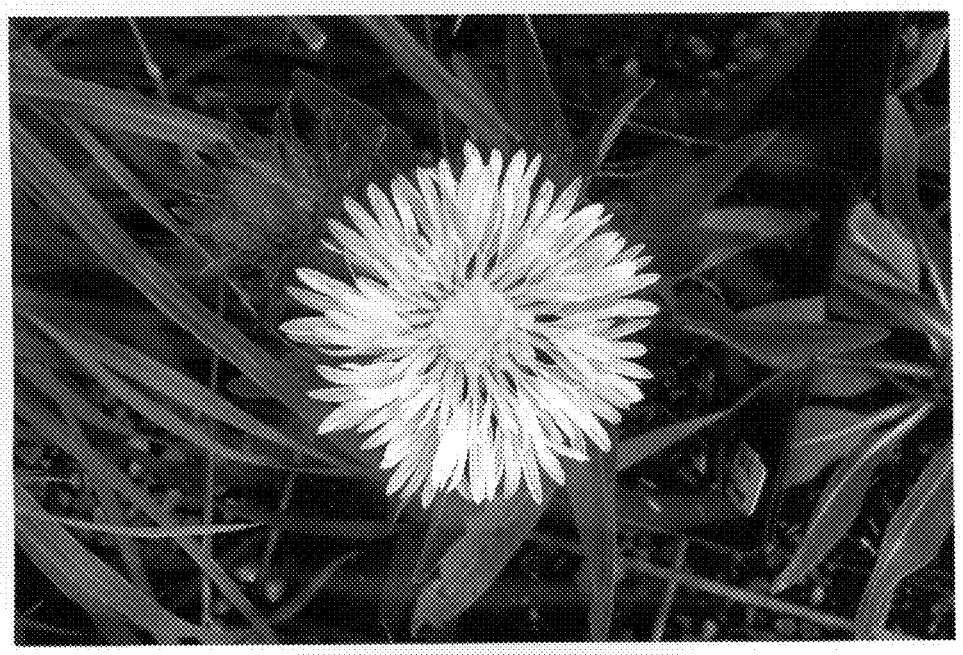

The photograph in FIG. 1 on the first sheet is a close-up of a new, young, 'Divinity' flower showing the yellow tinted center.

Figure 2:
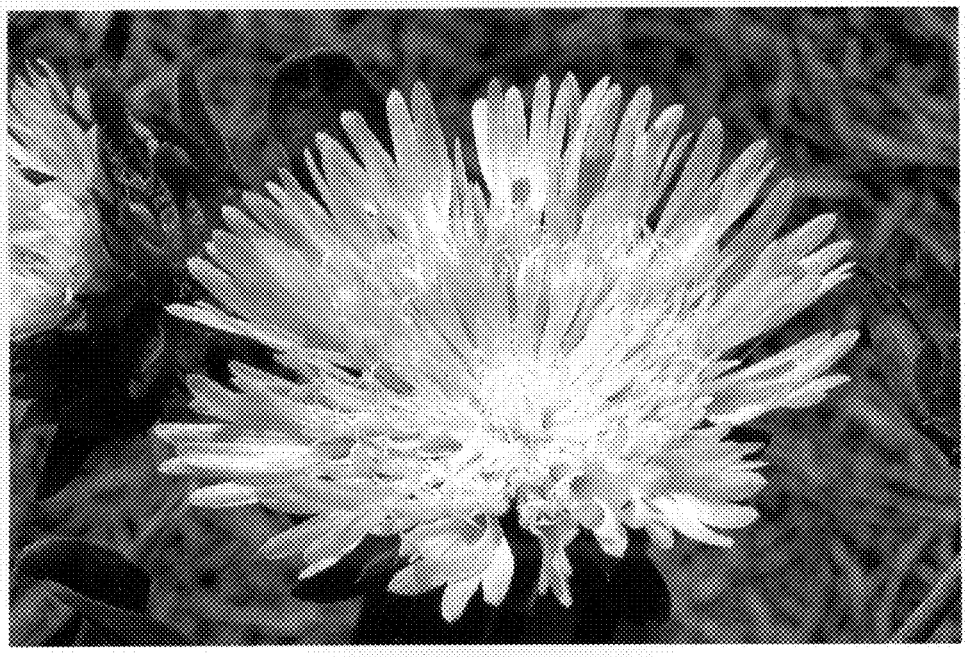

The photograph in FIG. 2 on the second sheet shows a mature 'Divinity' flower after the yellow tint has faded.

Figure 3:
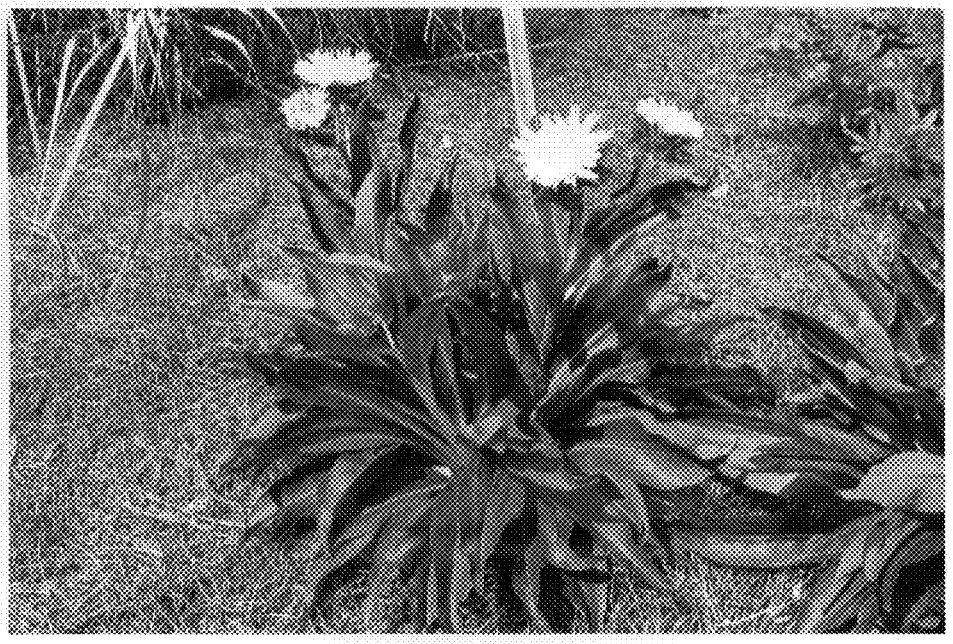

The photograph in FIG. 3 on the third sheet shows the growth habit of the new plant 'Divinity' as well as the strap like leaves and height of 'Divinity' flowers.

DETAILED BOTANICAL DESCRIPTION

The aforementioned photographs and following observations and measurements of the new *Stokesia* variety describe plants grown in full sun outdoor conditions in a trial garden located in Pensacola, Fla. The plants shown are eighteen weeks old. The following color references are based on the 2007 edition of The Royal Horticultural Society Colour Chart except when common dictionary terms are used.

Botanical classification: *Stokesia laevis* cultivar 'Divinity'.

Parentage: Chance seedling of *Stokesia laevis*.

Propagation:

*Method.*—By division and cuttings.

*Time to produce rooted plant.*—8-10 weeks.

*Finish time in a quart size pot.*—Four months.

*Root description.*—Fleshy.

*Rooting habit.*—Fibrous.

Plant description:

*Plant shape and habit.*—Herbaceous perennial with a uniform mounding habit. Flowering begins May and continues through fall.

*Plant size.*—Foliage height at flowering from soil line to the top of the leaves 30 to 35 cm and 50 to 55 cm wide at widest point.

*Plant growth rate.*—Moderate.

Foliage description:

*Arrangement.*—Basal, simple, semi-evergreen, fleshy, oblong—lanceolate to spatulate, margins are entire, apex is acute, base cuneate to attenuate. Midveins are impressed on upper surface and prominent on the underside.

*Foliage size.*—25 to 30 cm long; 4 to 5 cm wide.

*Foliage texture.*—Top surface is glaberous; Bottom surface is slightly glaucous.

*Color.*—Green Group N137A top surface and Green group 137B underside.

*Petiole.*—Leaves are sessile: Texture: glaberous; Color: Green Group N137A.

Flower description:

*Buds.*—4 to 5, 1.5 cm wide buds per inflorescence on 35 cm tall leafy stems (Green Group 143C), held above the foliage. Stems are 4.75 cm in diameter at the base and 0.5 cm distally. The peduncle is 4 to 13 cm long and wooly. The bracts are 2 to 3 cm long, Yellow-Green Group 146B, and number 30 to 40.

*Flowers.*—Single, perfect, radiate arranged in corymbs. Single flowers are 8 to 10 cm across. The corolla consists of 2 series of rays composed of 15 to 25 outer ray florets and are 3.5 to 5 cm long and 1.5 to 2.25 cm wide. Base is pleated and widens at the distal end with 5 lobes deeply cut. There are 70 to 90-disc florets, 2-3 cm long and 1 to 1.5 cm wide. Base is fluted and widens at the distal end with five lobes. Filaments are 1 cm long, Greyed Yellow group 161D. Anthers 0.2 to 0.3 cm long. Blooms are White Group 155B at the center and the rays are N155A. There is one pistil per each disc floret, 1-1.5 cm long. The ovary is inferior with a short style; stigma is two branched.

*Flowering.*—Normal flowering season begins early spring and continues intermittently through late fall. Flowers take 3 days to open and last 7-10 days. Fragrance is slightly sweet but insignificant.

Seed production: Achenes with 3 to 4 angles, 0.5 cm long, 0.2 cm wide, Grey-Brown Group 199C. Persistent pappus. Fruit set Heavy.

Disease resistance: Comparable to other members of this species.

Pests: No insect problems have been observed.

Temperature tolerance: USDA Zones 5-9.

What is claimed is:

1. A new and distinct cultivar of *Stokesia* plant named 'Divinity', as illustrated and described.

* * * * *